United States Patent [19]

Buchi et al.

[11] 4,028,278

[45] June 7, 1977

[54] CYCLOALIPHATIC UNSATURATED KETONES AS FRAGRANCE MODIFYING AGENTS

[75] Inventors: George H. Buchi; Hans Wuest, both of Cambridge, Mass.

[73] Assignee: Firmenich S.A., Geneva, Switzerland

[22] Filed: May 6, 1976

[21] Appl. No.: 683,939

Related U.S. Application Data

[60] Continuation of Ser. No. 532,649, Dec. 13, 1974, abandoned, which is a division of Ser. No. 281,220, Aug. 16, 1972, Pat. No. 3,890,370.

[30] Foreign Application Priority Data

Aug. 17, 1971 Switzerland ............ 12119/71

[52] U.S. Cl. ........................ 252/522; 260/586 R
[51] Int. Cl.² ............... C11B 9/00; C07C 49/48
[58] Field of Search ............ 252/522; 260/586 R

[56] References Cited

UNITED STATES PATENTS 2,933,506  4/1960  Osloff ........................ 260/343.2
3,822,315  7/1974  Klein et al. ................. 260/586 R
3,931,326  1/1976  Kovats et al. .................. 252/522
3,946,078  3/1976  Rauterstraucb ................. 252/522

FOREIGN PATENTS OR APPLICATIONS 1,240,309  7/1971  United Kingdom ............ 252/522

OTHER PUBLICATIONS

E. Demole et al., *Helv. Chim. Acta*, 53, pp. 541–551, 1970.

*Primary Examiner*—Veronica O'Keefe
*Attorney, Agent, or Firm*—Pennie & Edmonds

[57] ABSTRACT

New cycloaliphatic unsaturated ketones and their use as perfuming and odor-modifying agents in the manufacture of perfumes and perfumed products, and as flavoring and taste-modifying agents in the preparation of foodstuffs in general and imitation flavors for foodstuffs, beverages, animal feeds, pharmaceutical preparations and tobacco products.

Methods for preparing the said new compounds and certain of the starting materials used for their synthesis.

7 Claims, No Drawings

CYCLOALIPHATIC UNSATURATED KETONES AS FRAGRANCE MODIFYING AGENTS

This is a continuation of application Ser. No. 532,649, filed Dec. 13, 1974, now abandoned, which is a division of application Ser. No. 281,220, filed Aug. 16, 1972, now U.S. Pat. No. 3,890,379.

SUMMARY OF THE INVENTION

The invention relates to a new process for the preparation of unsaturated cycloaliphatic ketones having the formula

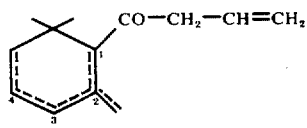

containing either two non-conjugated double bonds in the 1- and 4- positions, or two conjugated double bonds in the 1- and 3-, (exocyclic) 2- and 3-, or (endocyclic) 2- and 4- positions of the ring, the double bonds being represented by the dotted lines, which process comprises acylating organo-metallic compounds having the formula

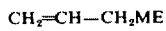

wherein ME represents a metal function, such as Li, Zn, Cd or Mg-halogen, by means of compounds having the formula

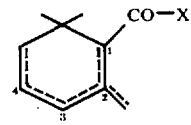

wherein the dotted lines have the same meaning as above and the symbol X represents a group which is reactive under the reaction conditions, e.g. halogen, O-CO-alkyl, O-CO-aryl, O-alkyl or O-aryl.

The invention relates further to certain of the said unsaturated cycloaliphatic ketones which are new compounds, and to certain of the starting materials or intermediates used for or formed during their syntheisis, as well as to the use of said compounds as fragrances and flavour-modifying agents.

The invention relates further to new processed for the preporation of unsaturated cycloaliphatic esters of formula

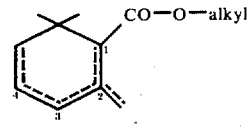

wherein the dotted lines have the meaning indicated above.

BACKGROUND OF THE INVENTION

One of the main objects of the aromatisation of foodstuffs for instance is to restore the original quality and nature of the flavour, aroma and taste of a given foodstuff material. Very often in fact the organoleptic properties of foodstuffs particularly diminish or are somehow modified in the course of the processes of freezing and storage, or during the modifications, such as cooking or baking, to which the foodstuffs are subjected in order to yield an edible material.

In the past the aromatisation was mainly achieved by using materials of natural origin. Nowadays, however, synthetic chemical compounds are used at an ever increasing rate. Said compounds possess the advantage of being available very often in unlimited quantities and at prices lower than those of the natural materials. Moreover, due to the fact that the flavouring character of a natural material is the result of the overall effect determined by the combination and interaction of each of its constituents, the effects achieved by said natural material are very often not as well reproducible as those obtained by the use of the pure synthetic compounds.

In the field of perfumery the man in the art has to solve a similar problem in attempting to reconstitute the olfactive notes of certain natural essential oils or extracts. The perfumer's creativity however is continually boosted by the finding of new synthetic compounds, the organoleptic properties of which will enable him to introduce unprecedented olfactive characters or nuances into new phantasy perfume compositions.

As a consequence, the problem that the chemical industry has to solve is to satisfy the increasing demand of new organoleptically interesting chemicals in order to better suit the specific needs of flavourists and perfumers.

It is known in the art that compounds of general formula

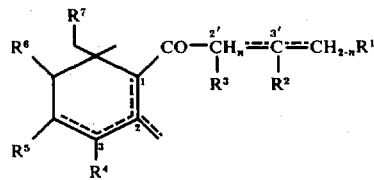

wherein
the side chain attached at position 1 of the ring contains one double bond in position 2' or 3'; the ring contains one endocyclic double bond in position 1 to 2,
or one exocyclic double bond in position 2, or two conjugated double bonds in position 1 and 3;
$n$ is zero or one;
$R^1$, $R^2$ and $R^3$ all represent hydrogen, or one of them an alkyl group and the others hydrogen; and
$R^4$, $R^5$, $R^6$ and $R^7$ all represent hydrogen, or one of them an alkyl group and the others hydrogen
possess valuable organoleptic properties [see e.g. Swiss Pat. No. 509,399 and German Offenlegungsschrift No. 2,022,216]. The present invention provides a similar class of compounds as well as processes for preparing them.

It has now been found in fact that most of the compounds of formula I and certain of their related derivatives, forming together a class of compounds of general formula

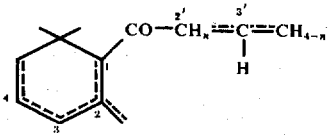

VIII

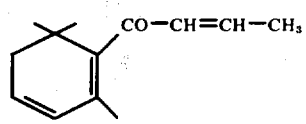

5 containing a double bond in the 2'-or 3'-position of the said chain and either two conjugated double bonds in the (endocyclic) 2- and 4-, or (exocyclic) 2- and 3-positions of the ring, or two non-conjugated doble bonds in the 1- and 4- positions of the ring, and wherein n stands for the integers 1 to 2, possess interesting organoleptic properties and accordingly they can be used as flavouring ingredients for modifying, enhancing or improving the organoleptic properties of foodstuffs for men and animals beverages, pharmaceutical preparations and tobacco products, and for the preparation of artificial flavouring compositions, and/or as perfuming agents for the preparation of perfumes and perfumed products.

Although the chemical structure of said new compounds is closely related to that of the known above mentioned cycloaliphatic ketones, we have surprisingly found that the olfactive and flavouring characters of the presently disclosed compounds are sensibly different from those possessed by the known derivatives. This fact confirms once more the character of unpredictability which is related to the phenomena of olfaction and taste perception. It has in fact to be underlined that in spite of the number of theories which have been put forward in order to understand the detection of the specific signaling obtained in the presence or in the absence of a given chemical, in the present state of our knowledge we have to admit that no theoretical explanation enables to predict with certainty the odour or taste of a chemical compound [see e.g.: G. Ohloff, La Recherche, 2 [18,], 1068; Molecular Structure and Organoleptic Quality, S.C.I. Monograph No. 1, (1975)]. In actual experience it is known for instance that the organoleptic properties of ambrinol of formula

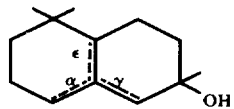

comprising a double bond at one of the positions indicated by the dotted lines, vary according to the specific position of said double bond in the molecule, the α-isomer possessing the most pronounced ambra character [see: Helv. Chim. Acta, 42, 2233 (1959)].

The particular position of the double bond as well as its ethylenic stereoisomerism in an open chain aldehyde, such as hexenal, have a determining effect on the odour. Pure cis-3-hexenal possesses in fact a very strong fresh green odour whereas trans-2-hexenal posseses a less defined sweet smell/Helv. Chim. Acta, 45, 2567 (1962)].

The new cycloapliphatic ketones of the present invention possess a distinct olfactive not reminiscent of the flowers of certain plants such as those of the family of mignonette with a characteristic fresh, rosy, green, heady note. The minty note of "β-damascenone", an analogous compound of formula

[see: Helv. Chim. Acta, 53, 541 (1970)], is still present in the odour of some of the new compounds of the invention, but its character is less harsh, definitely sweeter and it is reminiscent of the typical odour of the aromatic leaves or sage.

In addition depending on the nature of the products into which the compounds of the invention are incorporated they may develop a variety of notes such as aromatic, floral, wax-like, leather-like or terpenic notes or any desired combination of the said notes.

It has been found that the new compounds mentioned above increase the strength and the diffusion power of the perfume compositions to which they are added and impart thereto, in many cases, a very natural richness. In some cases, they impart to the products, in which they are incorporated, a taste of red berries and can be used for improving the taste and the artificial flavour of strawberry, cranberry, cherry, red-currants or analogous compositions. The new ketones can surprisingly be used for increasing the taste and flavour of products such as honey or red wine.

The proportions in which the new compounds can be used in order to produce an interesting odoriferous effect vary within wide limits. In the preparation of perfume compositions, for example, interesting effects can be obtained by the presence of the new compounds in ratios of about 100 ppm to 5% of the total of the composition. Depending on the desired odoriferous effects the ratios of these ketones can be increased to about 10% and even more.

If the new compounds are used as flavouring agents or as additives destined to modify the organoleptic properites of foodstuffs for men and animals, beverages, pharmaceutical preparations and tobacco, their ratios can also vary within wide limits.

Interesting flavouring effects can e.g. be obtained by the use of 0.1 to 10 ppm of the new compounds, based on the product to be flavoured. However, these ratios can be increased beyond 10 ppm and reach 100 ppm if it is desired to obtain special flavouring effects. In the preparation of flavouring compositions by admixture of the new compounds with other flavouring agents the said compounds can be used in ratios of about 0.1 to 15% of the total of the composition. In many cases the average of the ratios used lies between 1 and 10% of the total weight of the composition. It is to be understood that the limits of the proportions given above do not represent absolute limits; in certain cases where special effects are desired the new compounds can be used in higher or lower concentrations than those mentioned above.

The expression "foodstuff" is used in this specification in its broadest sense. It also comprises products such as coffee, tea and chocolate.

One of the processes of the invention for the preparation of unsaturated alicyclic ketones having the formula I comprises acylating organo-metallic compounds having the formula $$CH_2=CH-CH_2ME$$ II wherein ME represents a metal function, such as Li, Zn, Cd or Mg-halogen, by means of compounds having the formula

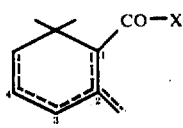

wherein the dotted lines have the same meaning as above and the symbol X represents a group which is reactive under the reaction conditions, e.g. halogen, O-CO-alkyl, O-CO-aryl, O-alkyl or O-aryl.

According to a specific embodiment of the present invention the lithium derivative of 2-propenyl is used as the organo-metallic compound, and an ester of formula

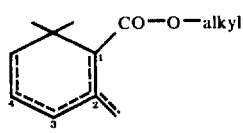

wherein the dotted lines have the meaning indicated above, is used as the compound of formula III. The alkyl radicals comprise e.g. methyl, ethyl, propyl, isopropyl, butyl, tert-butyl or iso-butyl radicals.

The compounds of formula III wherein the conjugated double bonds are in the 1- and 3-, (exocyclic) 2- and 3-, or (endocyclic) 2- and 4-positions of the ring, which are used as starting products in the process of the invention indicated above, can be prepared according to the process illustrated by the following scheme:

Gildemeister & Hoffmann, "Die Aetherischen Oele", IIId, pp. 137-8, Akademie Verlag, Berlin (1966).

The dehydrogenation can be carried out by first halogenating the cyclohexene ring in the allyl-position and then dehydrohalogenating the product of the said halogenation. Common halogenating reagents, e.g. haloamides such as N-bromosuccinimide, N-bromoacetamide, N-dimethyl-bromohydantoin and their chlorinated analogues, can be used as the halogenating agents.

N-bromosuccinimide is preferably used according to the usual method [see Chem. Rev., 63, 21 (1963)].

The halogenation in the allyl-position can be carried out in an inert solvent. A chlorinated solvent such as $CCl_4$, $CHCl_3$, $CH_2Cl_2$, dichloroethane, tetrachloroethane and trichloroethylene or a mixture of the said solvents can e.g. be used. The operation is preferably carried out at temperatures comprised between 20° and 100° C.

The dehydrohalogenation can be promoted by organic bases, e.g. tertiary amines such as morpholine, piperidine diethylaniline or dimethylaniline, and the dehydrohalogenation temperature is comprised between about 100° and 150° C.

According to the invention the compounds of formula IIIa, wherein the double bonds are in the (endocyclic) 2- and 4- positions of the ring, are prepared by a process which comprises treating an alkyl α-isopdroylidene-acetoacetate in an inert organic solvent with a compound resulting from the reaction of a guaternary phosphours salt having the formula $$[CH_2=CH-CH_2-PR_3]^+ X^-$$ IV wherein R represents an alkyl or aryl radical and X

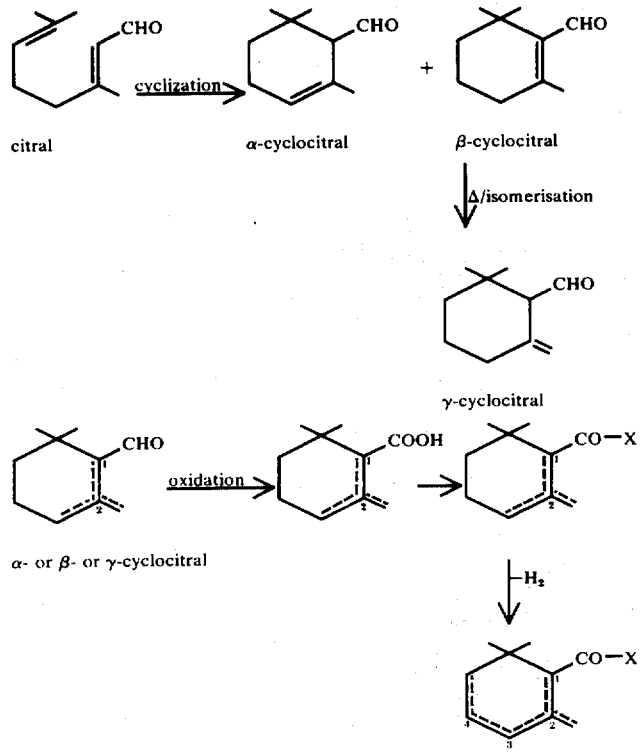

The cyclization of citral can be carried out by means of the usual techniques such as those described e.g. in represents a halogen such as e.g. chlorine, bromine or iodine, or a group such as e.g. $ClO_4$ or $BF_4$, with a strong base.

Allyl-triphenyl-phosphonium chloride or bromide are preferably used as the quaternary phosphorus salt, and n-butyl-, methyl- or phenyl-lithium as the strong base.

It has been observed that the nature of the base used as well so the reaction conditions selected have no considerable influence on the yield of the final product obtained. However, it is preferred to prepare the allyl-triphenyl- phosphonium chloride or bromide by the reaction of triphenuylphosphine with an excess of allyl chloride at reflux temperature (45° C). The treatment with a strong base can then be carried out at a temperature comprised between about —20° and about +20° C. n-Butyl-lithium is preferably used as the strong base, and the operation is carried out in an inert solvent such as ethers, e.g. ethyl ether, monoglyme, diglyme dioxan or tetrahydrofuran, or hydorcarbons, e.g. cyclohexane, hexane, benzene or toluene. Ethyl ether and hexane are preferably used.

According to the invention the compounds of formula IIIa, wherein the double bonds are in the 1- and 4- positions of the ring, having the formula

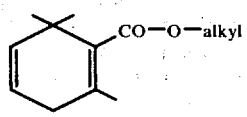

IIIa-4 are obtained by a process which comprises isomerizing a compound having the formula

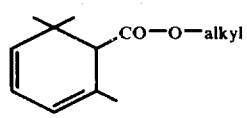

IIIa-1 by means of a basic isomerization agent.

Strong organic bases, e.g. alkali metal alkoxides such as sodium, potassium or lithium methoxide or ethoxide are preferably used as the basic agents.

The isomerization reaction is preferably carried out in an alcoholic medium and at a temperature in the vicinity of the reflux temperature of the chosen solvent.

When treating the compounds of formula IIIa-I with an acidic agent there is obtained a mixture comprising in addition to the starting product, the compounds having the formulae

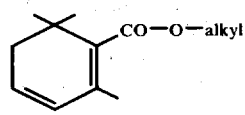 and 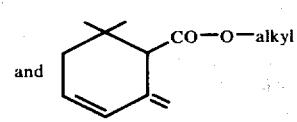

IIIa-2                IIIa-3

The separation of the constituents of the said mixture can be carried out by means of the techniques of separation commonly used in chemistry, e.g. by preparative vapour phase chromatography or by fractional distillation.

Strong organic or inorganic acids, e.g. p-toluenesulphonic aicd, or a hydrogen halide, e.g. hydriodic or hydrochloric acid, can be used as the acidic agent. The reaction is preferably carried out by mixing the compound which must be isomerized with the chosen reagent which is dissolved in a inert solvent, e.g. benzene, toluene, cyclohexane or hexane, and at a temperature in the vicinity of the boiling temperature of the selected solvent.

The compounds of formula IIIa can moreover be obtained from isophorone derivatives according to a process which can be illustrated by the following reaction scheme:

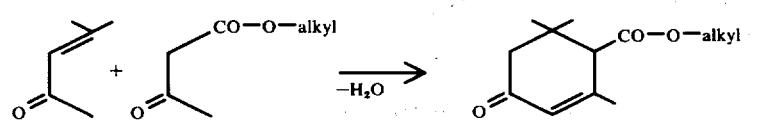

4-alkoxycarbonyl-isophorone

↓ reduction

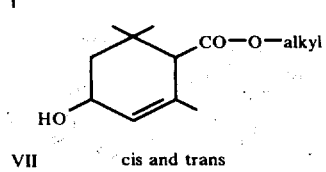

VII     cis and trans

↓ $-H_2O$

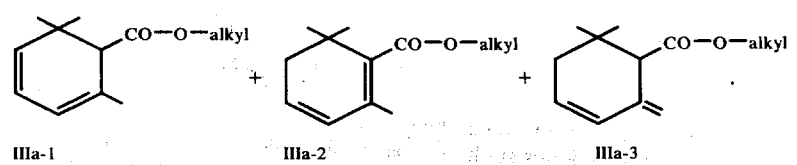

IIIa-1           IIIa-2           IIIa-3

The first step of the process illustrated above consists in a condensation between the mesityl oxide and an alkyl acetoacetate according to a known technique [see H. Rubinstein, J. Org. Chem. 27, 3886 (1962); J. D. Surmatis et al., J. Org. Chem., 35, 1053 (1970)].

The reduction of the 4-alkoxycarbonyl-isophorones can be carried out by means of reagents which are known to selectively reduce the carbonyl function to a secondary alcohol function, e.g. mixed hydrides of boron and an alkali metal, e.g. sodium or lithium [see e.g. H. O. House, "Modern Synthetic Reactions", Benjamin, Inc., New York (1965)].

a. epoxidizing a 4-alkoxycarbonyl-isophorone to yield a 3,3,5-trimethyl-4-alkoxycarbonyl-5,6-epoxy-cyclohexanone,
b. treating the resulting epoxy-ketone with hydrazine to yield a 1,3,3-trimethyl-2-alkoxycarbonyl-5-cyclohexen-1-ol, and
c. carrying out a rearrangement of the allyl double bond of the carbinol obtained according to (b) by means of an acidic agent.

The above process can be illustrated by the following scheme:

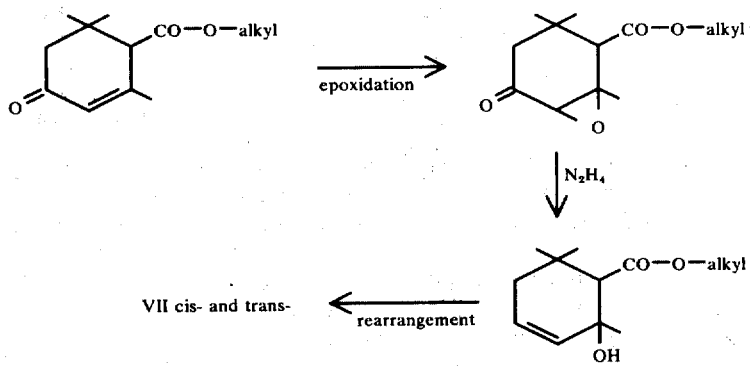

The carbinols prepared according to the process described above can be obtained in pure state by a separation by means of vapour phase chromatography or fractional distillation. However, for economic reasons, it is preferred to proceed to the subsequent dehydration of the mixture of isomers such as it is obtained directly by the described reduction in the presence of an acidic catalyst.

As the acidic dehydration catalyst a strong acid, e.g. phosphoric or sulphuric acid, if the preferred one.

The mixture comprising the cyclic esters IIIa, if subjected to fractional distillation or separation by means of vapour phase chromatography, yields the esters in a pure state. The latter can be used as starting products for the preparation of the compounds of formula I according to one of the processes of the invention, or can be reduced by means of lithium-aluminium hydride to their corresponding alcohols having the formulae

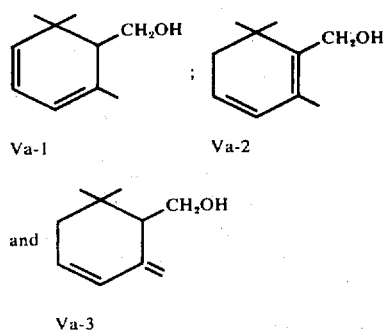

respectively.

According to a modification of the process described above the carbinols of formula VII can be prepared by a method which consists in The preparation of the epoxy derivative as well as its conversion into the corresponding tertiary alcohol can be carried out according to known techniques [cf. in this respect Tetrahedron, 19, 1091 (1963) and J. Org. Chem., 26, 3615 (1961)].

The subsequent allyl rearrangement can be carried out in an acidic agent such as an inorganic protonic acid e.g. sulphuric acid [cf. for example Ann. der Chem., 618, 202 (1958)].

According to another process of the invention compounds having the formula

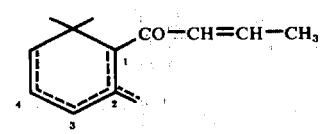

containing either two non-conjugated double bonds in the 1- and 4- positions, or two conjugated double bonds in the 1- and 3-, (exocyclic) 2- and 3-, or (endocyclic) 2- and 4- positions of the ring, the double bonds being represented by the dotted lines, are obtained by isomerization of the compounds of formula I by means of an acidic or basic isomerization agent, or by means of heat.

Thus, when treating the ketone having the formula

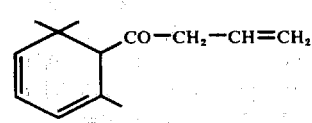

with a basic agent, e.g. with an alkali metal alkoxide, such as potassium tert-butoxide, the ketone of formula

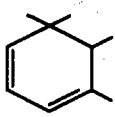

VIa is obtained.

If compound Ia is treated with an acidic isomerization agent, for example with a protonic acid such as p-toluenesulphonic acid, or a hydrogen halide such as hydriodic acid, or with acidic diatomaceous earth, there is obtained a ketone having the formula

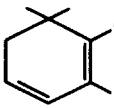

VIb

The isomerization of the double bond on the side chain is accompanied by a concomitant isomerization of the two conjugated double bonds of the hexadienic ring.

In particular, according to the process of the invention described above ketone VIb is obtained by the treatment of compounds having the formulae

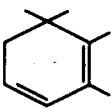

Ib or

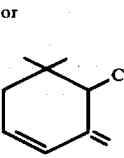

VIc with a basic or acidic isomerization agent.

The same reagents as those mentioned above in connection with the preparation of VIa and VIb can be used as the isomerization agents.

The said isomerization can be carried out by treating the compound to be isomerized and the reagent in a dissolved form in an inert organic solvent, e.g. and aliphatic or cycloaliphatic hydrocarbon, an aromatic hydrocarbon a chlorinated hydrocarbon, or an ester or an ether. Tetrahydrofuran is the preferred solvent.

As mentioned above, the class of compounds described in the present specification comprises new compounds. As such, 2,6,6-trimethyl-1-ethoxycarbonyl-1,4-cyclohexadiene, cis-and trans-2,6,6-trimethyl-1-[buten-2-oyl]-1,4-cyclohexadiene, 2,6,6-trimethyl-1-[buten-3-oyl]-1,4-cyclohexadiene, cis- and trans-2,6,6-trimethyl-1-[buten-2-oyl]-2,4-cyclohexadiene, 2,6,6-trimethyl-1-[buten-3-oyl]-2,4-cyclohexadiene, cis- and trans-2-methylene-6,6-dimethyl-1-[buten-2-oyl]-3-cyclohexene and 2-methylene-6,6-dimethyl-1-[buten-3-oyl]-3-cyclohexene should be mentioned.

The invention is illustrated in a more detailed manner by the following examples wherein the temperatures are indicated in degrees centigrade.

EXAMPLE 1

Preparation of
2,6,6-trimethyl-1-ethoxycarbonyl-2,4-cyclohexadiene, of
2,6,6-trimethyl-1-ethoxycarbonyl-1,3-cyclohexadiene and of
2-methylene-6,6-dimethyl-1-ethoxy-carbonyl-3-cyclohexene a. 21 g of 3,3,5-trimethyl-4-ethoxycarbonyl-5-cyclohexen-1-one were added dropwise to a suspension of 4 g of boron and sodium hydride in 100 ml of ethanol, maintained under vigorous stirring and at about 5°–10°. The reaction mixture was kept at room temperature overnight, concentrated to ⅓ of its original volume and neutralized by means of diluted hydrochloric acid.

The organic phase which separated was extracted with ether, and the ethereal extracts were then concentrated to dryness to yield a residue (19 g) which, by preparative vapour phase chromatography, gave cis- and trans-3,5,5-trimethyl-4-ethoxycarbonyl-5-cyclohexen-1-ol in a weight proportion of about 3:1 (yield 65%).

The two isomers have the following analytical characteristics:

A: $n_D^{20} = 1.4770$; $d_4^{20} = 1.020$
IR: 3400, 1725 cm$^{-1}$
NMR: 0.94 (6H,s); 1.22 (3H,t, J=7.5 cps); 1.62 (3H,s); 4.12 (2H); 4.1 (1H); 5.6 (1H) δ ppm
MS: M$^+$ = 212 (7); m/e: 197 (43); 183 (18); 166 (12); 154 (41); 138 (52); 123 (100); 109 (41); 98 (68); 83 (52); 69 (36); 55 (32); 43 (59); 29 (81).

B: $n_D^{20} = 1.4788$; $d_4^{20} = 1.038$
IR: 3400, 1720 cm$^{-1}$
NMR: 0.9 (3H,s); 1.09 (3H,s); 1.22 (3H,t, J=8 cps); 1.65 (3H,s); 2.23 (1H,m); 4.1 (2H,q, J=7 cps); 5.55 (1H,m) δ ppm
MS: M$^+$ = 212 (5); m/e: 197 (47); 183 (18); 166 (11); 151 (12); 138 (54); 123 (100); 109 (23); 98 (20); 83 (48); 69 (27); 55 (21); 43 (48); 29 (55).

b. 62 g of the mixture of isomers obtained according to the process described sub a. above were mixed with 0.5 g of p-toluenesulphonic acid in 200 ml of benzene and the resulting mixture was treated at boiling temperature in a water separator (2 hours). The reaction mixture was then treated with a diluted aqueous solution of sodium bicarbonate, washed with water until neutral, dried and distilled. A mixture comprising 2,6,6-trimethyl-1-ethoxycarbonyl-2,4-cyclohexadiene, 2,6,6-trimethyl-1-ethoxycarbonyl-1,3-cyclohexadiene and 2-methylene-6,6-dimethyl-1-ethoxycarbonyl-3-cyclohexene in a weight proportion of about 28 : 42 : 30, respectively, was obtained; b.p. 60°/0.01 Torr; 34.2 g.

The mixture of products thus obtained was distilled by means of a spinning band fractionating column and the components of the mixture were separated by means of vapour phase chromatography (column CARBOWAX).

2,6,6-Trimethyl-1-ethoxycarbonyl-2,4-cyclohexadiene:

$n_D^{20} = 1.4718$; $d_4^{20} = 0.9550$; b.p. about 42°/0.2 Torr.
IR: 1730, 1660, 1600, 730 cm$^{-1}$
NMR: 1.05 (6H,s); 1.2 (3H,t, J=7.5 cps); 1.72 (3H,s); 2.71 (1H,m); 4.06 (2H,q, J=7 cps); 5.0–5.75 (3H) δ ppm MS: $M^+ = 194$ (20); m/e: 194 (20); 179 (1); 165 (0.5); 151 (1); 133 (1); 121 (100); 107 (30); 105 (40); 91 (22); 77 (12); 65 (5); 53 (4); 65 (5); 53 (4); 39 (8); 19 (28).

2,6,6-Trimethyl-1-ethoxycarbonyl-1,3-cyclohexadiene:

$n_D^{20} = 1.4809$; $d_4^{20} = 0.9665$.

IR: 1720, 1635, 1585, 728 cm$^{-1}$

NMR: 1.08 (6H,s); 1.3 (3H,t, J=7 cps); 1.78 (3H,s); 4.15 (2H); 5.78 (2H,s) δ ppm MS: $M^+ = 194$ (30); m/e: 179 (4); 165 (2); 149 (36); 135 (7); 121 (100); 106 (98); 91 (35); 77 (15); 65 (5); 53 (4); 41 (9); 29 (58).

2-Methylene-6,6-dimethyl-1-ethoxycarbonyl-3-cyclohexene:

$n_D^{20} = 1.4809$; $d_4^{20} = 0.9585$

IR: 3080, 1725, 1630 and 888 cm$^{-1}$

NMR: 0.89 (3H,s); 0.98 (3H,s); 1.2 (3H,t, J=7.5 cps); 2.88 (1H,s); 4.87 (2H,m); 5.6–6.2 (2H) δ ppm MS: $M^+ = 194$ (13); m/e: 179 (1); 165 (1); 149 (2); 129 (8); 121 (100); 105 (37); 91 (19); 77 (13); 65 (4); 55 (5); 41 (13); 29 (26).

The 3,3,5-trimethyl-4-ethoxycarbonyl-5-cyclohexen-1-one used as starting product in the preparation described above can be prepared as follows:

260 g of ethyl acetoacetate were mixed with 200 g of mesityl oxide and 200 g of trifluoroboro-etherate in a vessel cooled externally by water and ice in order to maintain the temperature of the mixture at about 0°–5°. The said mixture is maintained at this temperature for 3 days, poured then onto ice (800 g) and neutralized with about 400 g of Na$_2$CO$_3$. Then it was extracted with ether and, after the usual treatments of separation, washing and drying, the combined organic extracts were concentrated. Distillation of the residue (135 g) gave 115 g of the desired product, b.p. 85°–90°/0.1 Torr, which has a purity of 80% as shown by analysis by means of vapour phase chromatography. The product can subsequently be purified by redistillation.

EXAMPLE 2

Preparation of
2,6,6-trimethyl-1-ethoxycarbonyl-2,4-cyclohexadiene, of
2,6,6-trimethyl-1-ethoxycarbonyl-1,3-cyclohexadiene and of
2-methylene-6,6-dimethyl-2-ethoxycarbonyl-3-cyclohexene a. 5 g of 3,3,5-trimethyl-4-ethoxycarbonyl-5-cyclohexen-1-one [which can be prepared according to the method described in Example 1] in 800 ml of methanol were cautiously mixed with a solution of 24 ml of a 30% solution of H$_2$O$_2$ and 6 ml of a 6N solution of NaOH. The reaction mixture, after having been stirred for 2 days at room temperature, was neutralized with a diluted HCl solution and the volatile portions were separated by evaporation. Distillation of the residue gave 3,3,5-trimethyl-4-ethoxycarbonyl-5,6-epoxycyclohexanone in a pure state.

B.p. 90°–5°/0.1 Torr; $n_D^{20} = 1.4673$; $d_4^{20} = 1.081$.

IR: 1715 cm$^{-1}$

NMR: 0.97 (3H,s); 1.28 (3H,s); 1.26 (3H,t, J=7.5 cps); 1.38 (3H,s); 2.21 (2H,s; 2.8 (1H,s); 3.03 (1H,s); 4.18 (2H,q, J=7 cps) δ ppm MS: $M^+ = 226$ (5); m/e: 211 (2); 197 (1); 181 (7); 165 (1); 151, (6); 138 (7); 119 (98); 117 (100); 98 (17); 63 (85); 69 (14); 55 (25); 43 (42); 29 (33).

b. 3 g of the epoxy-ketone obtained according to the process described sub a. above, dissolved in 20 ml of methanol, were added dropwise within 60 minutes to a mixture of hydrazine hydrate (6 ml) in 10 ml of methanol maintained at −10° and in a nitrogen atmosphere. The reaction mixture was then maintained at about 0° for one day, poured onto ice and extracted with ether. The combined organic extracts, after having been subjected to the usual treatments of drying and concentration, yielded 3 g of a residue which, by distillation, gave 1.7 g (yield 70%) of 1,3,3-trimethyl-2-ethoxycarbonyl-5-cyclohexen-1-ol.

$n_D^{20} = 1.4772$; $d_4^{20} = 1.031$.

IR: 3450, 1720 and 722 cm$^{-1}$

NMR: 1.02 and 1.04 (2×3H,s); 1.2 (3H,t, J=7 cps); 1.23 (3H,s); 2.57 (1H,s); 3.17 (1H,m); 4.08 (2H,q, J=7.5 cps); 5.51 (2H,m) δ ppm MS: $M^+ = 212$ (0.1); m/e: 197 (30); 179 (0.1); 167 (9); 151 (50); 139 (3); 121 (90); 101 (40); 83 (100); 69 (52); 55 (28); 43 (98); 29 (38).

c. A solution of 4.2 g of alcohol, prepared according to the process described in paragraph b. above, in 50 ml of tetrahydrofuran was diluted with water, and to the homogeneous solution thus obtained, maintained at −10°, there were added a few drops of 20% H$_2$SO$_4$. The reaction mixture was allowed to stand at room temperature for 24 hours, neutralized with a diluted aqueous solution of NaHCO$_3$ and extracted with petroleum ether. The combined organic extracts, after washing, drying and concentrating, yielded an oily residue (4 g) which, by separation by means of preparative vapour phase chromatography, gave a mixture of cis- and trans-3,5,5-trimethyl-4-ethoxy-carbonyl-5-cyclohexen-1-ol. The analytical data of the said compounds are identical with those shown by the carbinols prepared according to the process described in Example 1, paragraph a.

d. The subsequent conversion of the obtained carbinols into 2,6,6-trimethyl-1-ethoxycarbonyl-2,4-cyclohexadiene, 2,6,6-trimethyl-1-ethoxycarbonyl-1,3-cyclohexadiene and 2-methylene-6,6-dimethyl-1-ethoxycarbonyl-3-cyclohexene was carried out according to the same process as that described in Example 1, paragraph b.

EXAMPLE 3

2,6,6-Trimethyl-1-ethoxycarbonyl-2,4-cyclohexadiene

Method A. A solution of 1.6 M of n-butyl-lithium (43 ml; 77 millimoles) in hexane was added dropwise to a suspension of allyl-triphenylphosphonium, chloride (23.7 g; 70 millimoles) in 350 ml of anhydrous ether maintained at about 5°–10° in a nitrogen atmosphere and under vigorous stirring. Stirring was continued for about 1 hour and a solution of ethyl α-isopropylidene-acetoacetate (9.5g; 56 millimoles) in 50 ml of ether was then added to the reaction mixture. After having allowed the said mixture to stand for 1 hour at room temperature, water was added thereto, and the organic phase was separated. After washing, drying and concentrating, the organic phase yielded a partially crystalline residue.

After evaporation of the volatile portions the residue gave by successive extractions with hexane and purification through a column of aluminum oxide (50 g) 6.55 g of the desired ester (yield 60%) B.p. 93°/8 Torr.

IR : 1725, 1660 and 1600 cm$^{-1}$

NMR : 1.1 (6H,s); 1.3 (3H,t, J=7 cps); 1.8 (3H,s); 2.7 (1H,s); 4.1 (2H,q, J=7 cps); 5.2–5.8 (3H,m) δ ppm UV : 270 mμ (ε = 4220)

MS : m/e: 194 (17); 121 (100); 105 (38).

Method B. A solution of 1.6 M of methyl-lithium in ether (44 ml; 70 millimoles) was added dropwise to a suspension of allyl-triphenylphosphonium bromide (28.7 g; 75 millimoles) in 400 ml of hexane maintained at about 5°–10° in a nitrogen atmosphere and under vigorous stirring. The reaction mixture was maintained at room temperature for about 6 hours and then a solution of ethyl α-isoproylidene-acetoacetate (9.5 g; 56 millimoles) in 30 ml of hexane was added thereto dropwise. After having allowed the mixture to stand for 1 hour at room temperature it was filtered and the thus obtained solid substance was washed with a mixture of hexane and ether (2:1). The combined filtrates were then washed with water, dried and concentrated to yield a residue which was purified on a column filled with aluminium oxide (50 g) according to the method described in section A of this Example. There were thus obtained 7.51 g (69%) of the desired ester in a pure state. B.p. 95°/8 Torr.

The ethyl α-isopropylidene-acetoacetate used as starting product in the process described above can be prepared as follows:

To a solution of ethyl diacetyl-acetate maintained at 5°–10° [which can be prepared according to the method described in Helv. Chim. Acta, 35, 2280 (1952)] in 400 ml of anhydrous ether there were added 110 ml (0.33 mole) of a solution of 3 M methyl-magnesium bromide in ether. The reaction mixture was stirred for 24 hours at room temperature. After cooling, 50 ml of acetic acid anhydride were added and the whole was allowed to stand for 2 hours at room temperature, whereupon it was poured into ice-water. After separation, the organic phase was washed with a 5% aqueous solution of NaOH, then with water, whereupon it was dried (Na$_2$SO$_4$) and concentrated. The subsequent distillation of the residue yielded 16.1 g (63%) of ethyl αb.p. 94°–98°/8 Torr. A pure sample was obtained by purification of the said product by chromatography on a colum (silica gel and benzene) followed by vapour phase chromatography.

IR : 1730, 1700, 1640 and 1615 cm$^{-1}$

NMR : 1.3 (3H,t, J=7.5 cps); 1.9 (3H,s); 2.0 (3H,s); 2.15 (3H,s); 4.2 (2H,q, J=7.5 cps) δ ppm UV : 227 mμ (ε = 7900) MS : m/e: 170 (16); 96 (100); 43 (98).

The allyl-triphenylphosphonium chloride used as starting product in the process described above can be prepared as follows:

52.5 g of triphenylphosphine in 300 ml of allyl chloride were refluxed for 96 hours. A solid crystalline product was obtained, m.p. = 221°–227° . IR : 2450, 2320, 1635, 1585, 985 and 930 cm$^{-1}$ NMR (CDCl$_3$) : 4.9 (2H,d of d, J=15 and 5 cps); 5.2–5.9 (3H); 7.7–8.2 (15H) Δ ppm.

The corresponding bromide can be prepared according to the method described by H.O. House et al., J. Org. Chem., 30, 1061 (1965).

EXAMPLE 4

2,6,6-Trimethyl-1-ethoxycarbonyl-1,4-cyclohexadiene 1.0 g of 2,6,6-trimethyl-1-ethoxycarbonyl-2,4-cyclohexadiene was added to a solution of 0.5 M soduim ethoxide in ethanol, maintained in a nitrogen atmosphere and under vigorous stirring. The reaction mixture was refluxed for 60 minutes, then a few drops of acetic acid were added thereto. After evaporation of the volatile portions, the mixture was extracted with pentane and the combined organic extracts were subjected to the usual treatments of washing, drying (Na$_2$SO$_4$) and concentration. Distillation of the thus obtained residue yielded 0.92 g of a mixture 55:45 of the isomers 2,6,6-trimethyl-1-ethoxycarbonyl-2,4- and -1,4-cyclohexadiene B.p. 92°/8 Torr.

An analytical sample was obtained by vapour phase chromatography.

IR : 1705 and 1640 cm$^{-1}$

NMR : 1.1 (6H,s); 1.3 (3H,t, J=7 cps); 1.7 (3H,s); 2.6 (2H,s); 4.2 (2H,q, J=7 cps); 5.4 (2H,m) δ ppm UV : 232 mμ (ε = 1320)

MS : m/e: 194 (100); 107 (100); 91 (32).

EXAMPLE 5

2,6,6-Trimethyl-1-[buten-3-oyl]-2,4-cyclohexadiene
and
2-methylene-6,6dimethyl-1-[buten-3-oyl]-3-cyclohexene 2 ml of a solution of 9.4 g (70 millimoles) of allylphenyl ether in 10 ml of ether were added to a suspension cooled to 0° and maintained under nitrogen, of 2.4 g (0.35 g-atom) of finely cut lithium in 40 ml of anhydrous tetrahydrofuran. Previously a few crystals of diphenyl had been added to the said suspension. After the appearance of a greenish colour, the residual solution of allyl-phenyl ether was added dropwise to the reaction mixture maintained at about −15°. Cooling was continued for about 30 more minutes. The resulting solution of ally-lithium was withdrawn from the reaction vessel by means of a syringe and slowly added to a solution of 2,6,6-trimethyl-1-ethoxycabonyl-2,4-cyclochexadiene, maintained under stirring, [which can be prepared according to the process described in Example 1](3.88 g; millimoles) in 40 ml of ether at −60° and in a nitrogen atmosphere. The reaction mixture, after having been heated to room temperature, was poured into ice water and extracted twice with pentane. The combined extracts were washed with water, dired over anhydrous Na$_2$SO$_4$ and concentrated to yield a residue which, by fractional distillation, gave 3.19 g (84%) of trans-2,6,6-trimethyl-1-[buten-3-oyl]-2,4-cyclohexadiene; b.p. 41°–43°/0.05 Torr.

An analytical sample was prepared by purification by means of chromatography on a column filled with silicic acid and using hexane containing 2% of ethyl acetate as the eluant.

IR : 1695, 1650, 1590, 990 and 915 cm$^{-1}$

NMR : 1.0 (3H,s) 1.1 (3H,s); 1.7 (3H,s); 2.6 (1H,s); 3.2 (2H,d, J=7 cps); 4.7–6.1 (6H,m) δ ppm UV : 267 mμ (ε = 3900)

MS : m/e: 190 (7); 121 (100); 105 (44).

By applying the same procedure as indicated above to the acylation of allyl lithium by 2-methylene-6,6-dimethyl-1-ethoxycarbonyl-3-cyclohexene [prepared according to Example 1], there will be obtained 2- methylene-6,6-dimethyl-1 -[buten-3-oyl]-3-cyclohexane.

IR : 1650–1690, 1590, 970 cm⁻¹
MS : M⁺= 190.

EXAMPLE 6 trans-2,6,6-Trimethyl-1-[buten-2-oyl]-2,4-cyclohexadiene and
trans-2-methylene-6,6-dimethyl-1-[buten-2oyl]-3-cyclohexene 2.46 g of 2,6,6-trimethyl-1-[buten-3-oyl]-2,4-cyclohexadiene [prepared according to the process described in Example 5] were added to a solution of 140 mg of potassium in 40 ml of tert-butanol maintained in a nitrogen atmosphere. After having allowed the reaction mixture to stand for 5 minutes at room temperature, a few drops of acetic acid were added thereto, and the volatile portions were then eliminated by evaporation under reduced pressure. Water was added to the concentrated mixture thus obtained and it was extracted with pentane. After separation, the organic extracts were washed, dried over $Na_2SO_4$, evaporated and gave a residue which, by fractional distillation, yielded 1.76 g (72%) of the desired ketone. B.p. 39°/0.04 Torr.

IR: 1680, 1650, 1620, 1590 and 965 cm⁻¹
NMR : 0.95 (3H,s); 1.0 (3H,s); 1.7 (3H,s); 1.8 (H, d of d, J = about 1 and 7 cps); 2.6 (1H,s); 5.2–7.0 (5H,m) δ ppm
UV : 235 mμ ($\epsilon$ = 10500); 266 ($\epsilon$ = 4650)
MS: m/e: 190 (8) 121 (71); 96 (100).

By applying the same procedure as that indicated above to the isomerization of 2-methylene-6,6-dimethyl-1-[buten-3-oyl]-3-cyclohexene [prepared according to the process described in Example 5], there will be obtained trans-2-methylene-6,6-dimethyl-1-[buten-2-oyl]-3-cyclohexene.

IR : 3080, 1600-1690, 960, 880 cm⁻¹
SM : M⁺ = 190
NMR : 0.90 (3H,s); 0.95 (3H,s); 1.90 (3H, d of d, J=6.5, J' = ca. 1 cps); 2.00 (2H,m); 310 (1H,s); 4.80 (1H,s); 5.10 (1H, d, J=10 cps); 6.05 (1H, d of q, J=16 and J' = ca. 1 cps); 6.75 (1H, d of q, J=16, J'=6.5 cps) δ ppm
UV = λEtOH/max = 230 mμ ($\epsilon$ = 24000).

EXAMPLE 7 trans-2,6,6-Trimethyl-1-[buten-2-oyl]-1,3-cyclohexadiene

A mixture of 289 mg of trans-2,6,6-trimethyl-1-[buten-2-oyl]-2,4-cyclohexadiene [prepared according to the process described in Example 6], 25 mg of p-toluenesulphonic acid and 4 ml of anhydrous benzene were refluxed for 2 hours. The reaction mixture was then diluted with pentane, the combined organic extracts were washed with a 5% solution of sodium bicarbonate and water, dried over $Na_2SO_4$ and concentrated. The resulting oily residue was distilled under reduced pressure (0.1 Torr; at a bath temperature of about 80°) to yield 201 mg of a mixture containing 33% of trans-2,6,6-trimethyl-1-[buten-2-oyl]-1,3-cyclohexadiene.

An analytical sample was obtained by purification by means of preparative vapour phase chromatography. The analytical data were identical with these shown by a sample prepared by known methods [see for example French Pat. No. 1,591,031].

EXAMPLE 8 trans-2,6,6-Trimethyl-1-[buten-2-oyl]-1,3-cyclohexadiene

A solution of allyl-lithium in ether [prepared as described in Example 5 from 1.2 g of lithium and 4.7 g of allyl-phenyl ether] was added to a solution of 2.02 g (10.4 millimoles) of 2,6,6-trimethyl-1-ethoxycarbonyl-1,3-cyclohexadiene in 20 ml of ether at —60°. The reaction mixture is treated in a manner analogous to that described in Example 5 and yielded 1.96 g of a product of b.p. 44°–46° 0.05 Torr. The analysis by means of NMR showed that the thus obtained product comprised trans-2,6,6-trimethyl-1-[buten-2-oyl]- and 2,6,6-trimethyl-1-[buten-3-oyl]-1,3-cyclohexediene in a ratio of 1:2, respectively.

By isomerizing the said mixture according to the method indicated in Example 6 by means of a solution of 25 mg of potassium in 30 ml of tert.-butanol there were obtained 1.70 g (86%) of the desired product. B.p. 51°/0.08 Torr.

IR : 1665, 1630, 1610 cm⁻¹
NMR : 1.0 (6H,s); 1.6 (3H,s); 1.9 (3H,d of d, J = about 1 and 7 cps); 2.1 (2H, d, J= about 2 cps); 5.7–7.1 (4H,m) δ ppm
UV : 228 mμ ($\epsilon$ = 12000); 255 mμ ($\epsilon$ = 5000); 310 mμ $\epsilon$ = 2000)
MS : m/e: 190 (19); 121 (100); 69 (62).

EXAMPLE 9

2,6,6-Trimethyl-1-ethoxycarbonyl-1,3-cyclohexadiene

A mixture of 2.0 g of 2,6,6-trimethyl-1-ethoxycarbonyl-2,4-cylohexadiene [prepared according to the process indicated in Example 1], 100 mg of p-toluenesulphonic acid and 25 ml of anhydrous benzene were refluxed for 4 hours in a nitrogen atmosphere. The resulting solution was diluted with pentane, washed with a 5% solution of sodium bicarbonate, then with water, and then dried over $Na_2SO_4$ and concentrated.

The resulting residue was distilled to yield a product of b.p. 96°/8 Torr; 1.87 g (93%). By vapour phase chromatography (silicone) there were obtained three isomeric esters in a ratio by weight of 20 : 22 : 58, respectively, represented by the formulae

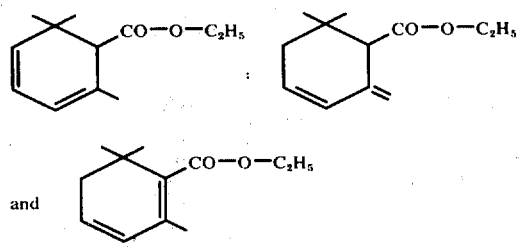

The said esters have the analytical characteristics which are shown in Example 1.

EXAMPLE 10 trans-2,6,6-Trimethyl-1-[buten-2-oyl]-1,4-cyclohexadiene

By following the same procedure as that indicated in Example 5 about 1 ml of a solution of 4.7 g (35 millimoles). of allyl-phenyl ester in 5 ml of ether is treated with a suspension of 1.25 g (0.18 g-atom) of lithium in 30 ml of anhydrous tetrahydrofuran. After the appearance of a greenist colour, the residual allyl-phenyl ether solution was added dropwise to the reaction mixture maintained at about −15°. Proceeding in the manner described in Example 5, the resulting allyl-lithium solution was withdrawn from the reaction vessel by means of a syringe and slowly added to a solution of 2.03 g (10.4 millimoles) of 2,6,6-trimethyl-1-ethoxycarbonyl-1,4-cyclohexadiene, maintained under stirring [which can be prepared according to the process described in Example 4], in 40 ml of ether at −60° and in a nitrogen atmosphere. The reaction mixture was heated to room temperature, poured into ice water and twice extracted with pentane. The combined extracts were washed with water, dried over $Na_2SO_4$ and concentrated. The resulting residue was added in a nitrogen atmosphere to a solution of 50 mg of potassium tert-butoxide in 30 ml of tert-butanol. After having maintained the mixture at room temperature for 10 minutes, a few drops of acetic acid were added thereto, whereupon the volatile portions were evaporated under reduced pressure, Then water was added to the reaction mixture and it was extracted with pentane. The organic extracts were separated, combined and treated according to the usual methods of washing with water, drying over $Na_2SO_4$ and concentration. The resulting oil was purified by chromatography on a column (70 g of silicic acid; hexane/1% ethyl acetate).

There were thus obtained 1.43 g (73%) of the desired product; b.p. 62°10.15 Torr.

IR ($CHCl_3$) : 1675, 1640, 1630, 1615, 975 cm$^{-1}$

NMR ($CCl_4$) : 1.0 (6H,s); 1.5 (3H,s); 1.9 (3H, d of d, J=1 and 7 cps); 2.6 (2H, s broad); 5.3–7.0 (4H,m) δ ppm UV (ethanol): 228 mμ (ε = 12900).

EXAMPLE 11

A base perfume composition for after-shave lotion has been prepared by admixing the following ingredients (parts by weight):

| | |
|---|---|
| Menthol | 10 |
| Eugenol | 50 |
| Coumarine | 20 |
| Muscone at 10 %* | 20 |
| Phenyl ethyl alcohol | 120 |
| Lavender oil | 210 |
| Pimento oil | 40 |
| Cinnamon oil | 5 |
| Synth. bergamot | 270 |
| Cyclopentadecanone at 10 %* | 30 |
| Methyl 2-pentyl-3-oxo-cyclopentyl acetate | 20 |
| Absolute oak moss | 15 |
| Benzyle salicylate | 20 |
| Isobutylsalicylate | 30 |
| Geranium Bourbon oil | 70 |
| Musk ketone | 20 |
| Ethyl alcohol | 50 |
| | 1000 |

*in 95 % ethyl alcohol

By adding to 95 g of the hereinabove given base composition 5 g of 2-methylene-6,6-dimethyl-1-[buten-2-oyl]-3-cyclohexene there is obtained a perfume composition possessing a pleasant and fresh woody, leathery note. An analogous effect is observed by adding in the same proportion to the above given base composition 2-methylene-6,6-dimethyl-1-[buten-3-oyl]-3-cyclohexene.

EXAMPLE 12

A base perfume composition has been prepared by admixing the following ingredients (parts by weight):

| | |
|---|---|
| Musk ketone | 10 |
| Dodecanal at 10 % | 20 |
| Undecanal at 10 %* | 10 |
| Angelica roots at 10 %* | 20 |
| Methyl 2-pentyl-3-oxo-cyclopentyl acetate at 10 %* | 50 |
| Ylang | 30 |
| Hydroxycitronellal | 20 |
| Galbanum oil | 10 |
| Coriandre oil | 40 |
| Cedar oil | 70 |
| Eugenol | 50 |
| Amyl salicylate | 40 |
| Citronellol | 50 |
| Isomethyl ionone | 50 |
| Citral | 10 |
| Vetyveryl acetate | 20 |
| Lavender oil | 60 |
| Geranium Bourbon oil | 80 |
| Absolute oak moss at 50 %* | 20 |
| Brazil mint oil | 20 |
| Artificial Bergamot | 100 |
| Artificial Neroli | 90 |
| Phenyl ethyl alcohol | 100 |
| Diethylphthalate | 20 |
| | 1000 |

*in diethyl phthalate

By adding to 90 g of this mixture 10 g of 2,6,6-trimethyl-1-[buten-2-oyl]-1,4-cyclohexadiene there will be obtained a composition possessing a better diffusion than the base composition. The obtained composition possesses a natural herbal tonality.

An analogous effect is observed by adding in the same proportions given to the above base composition 2,6,6-trimethyl-1-[buten-3-oyl]-1,4-cyclohexadiene.

EXAMPLE 13

Perfume Composition of the "Chypre" Type

A perfume composition of the "Chypre" type was obtained by admixing the following ingredients (parts by weight):

| | |
|---|---|
| Bergamot | 21 |
| Sweet orange oil | 0.5 |
| Synthetic neroli | 1 |
| Synthetic rose | 9 |
| Synthetic jasmin | 9 |
| Ylang extra | 6 |
| Methylionone | 6 |
| Hydroxycitronellal | 6 |
| Santal oriental | 3 |
| Patchouli | 1.5 |
| Vetyveryl acetate | 4.5 |
| Natural degreased civet, 10 %* | 3 |
| Labdanum ciste absolute, 10 %* | 2 |
| Musk ketone | 4 |
| 1,1-Dimethyl-6-tert-butyl-4-acetyl-indane | 0.5 |
| Coumarin | 3 |
| Trichloromethylphenylcarbinyl acetate | 1.5 |
| Tarragon, 10 %* | 3 |
| Oak moss absolute, 50 %* | 6 |
| Benjoin resinoid, 10 %* | 1.5 |
| Cinnamic alcohol of Styrax | 1.5 |
| Jasmin absolute | 1.5 |
| Rose absolute | 1 |
| Cyclopentadecanolide, 10 %* | 2 |
| Methylnonylacetic aldehyde | 1.5 |

*in ethyl phthalate

By adding to 99.5 g of this mixture 0.5 g of a 10% solution of trans-2,6,6-trimethyl-1-[buten-2-oyl]-2,4-cyclohexadiene there will be obtained a more powerful composition than the basic composition whose diffusion is improved and which presents a very natural richness. Analogous results are obtained by replacing in the above example trans-2,6,6-trimethyl-1-[buten-2oyl]-2,4-cyclohexadiene by 2,6,6-trimethyl-1-[buten-3-oyl]-2,4-cyclohexadiene.

EXAMPLE 14

Perfume Composition of the "Floral" Type

A composition of the "Floral" type is prepared by admixing the following ingredients (parts by weight):

| | |
|---|---|
| Decanal, 10 %* | 1 |
| Undecylenic aldehyde, 10 %* | 2 |
| Lauric aldehyde, 10 %* | 1 |
| Methylnonylacetic aldehyde, 10 %* | 0.5 |
| Synthetic lily of the valley | 16.5 |
| Synthetic lilac | 3 |
| Synthetic rose | 7 |
| Synthetic jasmin | 12 |
| Bergamot | 6 |
| Tarragon, 10 %* | 3 |
| Ylang extra | 9 |
| Synthetic carnation | 6 |
| Methylionone | 6 |
| Vetiveryl acetate | 4 |
| Santalol | 2 |
| Oak moss absolute, decolourized, 10 %* | 3 |
| Natural civet, degreased, 10 %* | 3 |
| Lily absolute, 1 %* | 2 |
| Orange blossom absolute, 10 %* | 2 |
| Jasmin absolute | 2 |
| Rose absolute | 1 |
| Musk ketone | 4 |
| Trichloromethylphenylcarbinyl acetate | 2 |
| Tolu balm absolute, colourless, 10 %* | 1.5 |

*in diethyl phthalate

By adding to 98 g of this mixture 2 g of a solution of trans-2,6,6-trimethyl-1-[buten-2-oyl]-2,4-cyclohexadiene at 10% in diethylphthalate there will be obtained a more powerful composition than the basic composition whose diffusion is improved and which has a very natural richness. The composition thus obtained possessed a fresh green note with a lifting character.

Similar results were achieved by adding to the same base composition in the proportions indicated a solution of 2,6,6-trimethyl-1-[buten-3-oyl]-2,4-cyclohexadiene.

EXAMPLE 15

Perfume Composition of the "Floral" Type

A composition of the "Floral" type is prepared by admixing the following ingredients (parts by weight):

| | |
|---|---|
| Rhodinol | 24 |
| l-Citronellol | 21 |
| Chemically pure geraniol | 12 |
| Phenylethyl alcohol | 24 |
| Linalool | 2.5 |
| Farnesol | 2 |
| Eugenol | 0.5 |
| Methyleugenol | 2 |
| Musk ketone | 4 |
| 1,1-Dimethyl-6-tert.butyl-4-acetyl-indane | 0.5 |
| Coumarin | 3 |
| Trichloromethylphenylcarbinyl acetate | 1.5 |
| Tarragon, 10 %* | 3 |
| Oak moss absolute, 50 %* | 6 |
| Benjoin resinoid, 10 %* | 1.5 |
| Cinnamic alcohol of Styrax | 1.5 |
| Jasmin absolute | 1.5 |
| Nonanal, 10 %* | 0.5 |
| Decanal, 1 %* | 2 |
| Undecanal, 10 %* | 0.5 |
| Deterpenated geranium oil | 1.5 |
| Phenylethyl salicylate | 0.5 |

*in diethyl phthalate

By adding to 98.5 g of this mixture 1.5 g of trans-2,6,6-trimethyl-1-[buten-2-oyl]-2,4-cyclohexadiene there will be obtained a more powerful composition than the basic composition whose diffusion is improved and which has a very natural richness. Similar effects were achieved by adding to the same base composition in the identical proportions 2,6,6-trimethyl-1-[buten-3-oyl]-2,4-cyclohexadiene.

EXAMPLE 16

Preparation of a Flavouring Composition for Liqueurs of the "Abbatial" Type

A flavouring composition destined for the preparation of liqueurs of the "abbatial" (or "chartreuse") type is prepared by admixing the following ingredients (parts by weight):

| | |
|---|---|
| Neroli oil | 5 |
| Clove oil | 20 |
| Cardamom oil | 25 |
| Nutmeg oil | 25 |
| Cinnamon oil | 25 |
| Lemon oil | 35 |
| Sweet orange oil | 65 |
| Angelica grain oil | 75 |
| Peppermint oil | 75 |
| Bitter orange oil | 200 |
| Angelica root oil | 445 |
| Total | 995 |

A "test" composition is prepared by the addition of 5 g of trans-2,6,6-trimethyl-1-[buten-2-oyl]-2,4-cyclohexadiene to 995 g of the above mixture. The "check" mixture results from the addition of 5 g of Angelica root oil to 995 g of the above mixture.

A base for liqueur is prepared by admixing the following ingredients in the doses indicated:

| | |
|---|---|
| Edible alcohol, 96 % (v/v) | 325 ml |
| Wine spirit, 74 % | 100 ml |
| Sugar syrup, 65 % | 10 ml |
| Water | 565 ml |
| Total | 1000 ml |

The base is flavoured with 10 g of flavouring composition per 100 g of base. The prepared and finished liqueurs are tasted by a group of experts. All the members of the group have declared that the "test" liqueur possessed a more rounded-off taste than that of the "check" liqueur.

EXAMPLE 17

Preparation of a flavouring composition of the "Tutti-Frutti" type

A flavouring composition of the "Tutti-Frutti" type was prepared by admixing the following ingredients (parts by weight):

| | |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |
| Total | 975 |

25 g of trans-2,6,6-trimethyl-1-[buten-2-oyl]-2,4-cyclohexadiene were added to 975 g of the above mixture called "test" composition. A "check" composition was prepared by the addition of 25 g of lemon oil to 975 g of the above mixture.

The "test" and "check" compositions were added to the foodstuffs described below in the indicated proportions (100 g of product to be flavoured):

| Cake | 20 g |
| Custard | 5 – 10 g |
| Candy | 15 – 20 g |

Candy: 100 ml of sugar syrup (obtained by dissolving one kilogram of sucrose in 600 ml of water) and 20 g of glucose were mixed and slowly heated to 145°. The flavour was added to the mass and the mixture was allowed to cool and harden.

Custard: A mixture of 60 g of sucrose and 3 g or pectin were added, while stirring, to 500 ml of warm milk. The mixture was brought to the boiling point for a few seconds and the flavour was added, whereupon the whole was cooled.

Cake: The following ingredients were mixed: 100 g of vegetable margarine, 1.5 g of NaCl, 100 g of sucrose, 2 eggs and 100 g of flour. The flavour was added to the above mass and the whole was heated to 180° for 40 minutes.

The samples of finished foodstuff were tasted by a group of experts who had to state their opinion as to the taste of the samples which had been submitted to them. All the members of the group unanimously declared without any hesitation that the "test" samples had a more marked fruity and woody note than that of the "check" samples and that they moreover possessed a character which was reminiscent of red berries.

Analogous results were obtained by replacing in the above example trans-2,6,6-trimethyl-1-[buten-2-oyl]-2,4-cyclohexadiene by 2,6,6-trimethyl-1-[buten-3-oyl]-2,4-cyclohexadiene, cis- and trans-2-methylene-6,6-dimethyl-1-[buten-2-oyl]-3-cyclohexene, 2-methylene-6,6-dimethyl-1-[buten-3-oyl]-3-cyclohexene, cis- and trans-2,6,6-trimethyl-1-[buten-2-oyl]-1,4-cyclohexadiene or 2,6,6-trimethyl-1-[buten-3-oyl]-1,4-cyclohexadiene.

EXAMPLE 18

A base flavouring composition was prepared by admixing the following ingredients (parts by weight):

| Wine fusel oil | 10 |
| Hex-3-enol | 10 |
| p-Methyl-acetophenone | 65 |
| α-Ionone at 10 %* | 5 |
| Geranyl acetone | 15 |
| Hexahydropseudoionone | 5 |
| Rum | 380 |
| Ethyl alcohol (95 %) | 510 |
| | 1000 |

*in 95 % ethyl alcohol 10 g of a solution at 1% of the above composition in 95% ethyl alcohol were sprayed on 100 g of a tabacco mixture of "american blend" type (sample C or "control").

A "test" sample (T) was prepared by spraying on 100 g of a tobacco mixture of "american blend" type a flavouring composition prepared by adding to 99 g of the above base composition 1 g of 2,6,6-trimethyl-1-[buten-2-oyl]-2,4-cyclohexadiene.

The two tobacco samples thus prepared were used for the preparation of cigarettes the smoke of which was subsequently subjected to taste evaluation by a panel of trained tasters.

The taste and flavour of the cigarettes prepared with tobacco sample T was characterized by a burnt note and by a woody, herbal character reminiscent of hay. These latter features were not shown by the cigarettes prepared with tobacco sample C.

We claim:

1. A perfume composition which comprises as one of its active ingredients, for enhancing, improving or modifiying its floral or fruity character, a small but effective amout of a compound having the formula

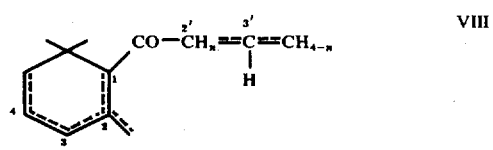

containing a double bond in the 2'- or 3'-position of the side chain and either two conjugated double bonds in the (endocyclic) 2- and (endocyclic) 4-, or (exocyclic) 2- and 3- positions of the ring, or two non-conjugated double bonds in the 1- and 4-positions of the ring, the double bonds being represented by the dotted lines, and whereas n stands for the integers 1 or 2.

2. The perfume composition of claim 1 wherein the compound is cis- and trans-2,6,6-Trimethyl-1-[buten-2-oyl]-1,4-cyclohexadiene.

3. The perfume composition of claim 1 wherein the compound is cis- and trans-2,6,6-Trimethyl-1-[buten-2-oyl]-2,4-cyclohexadiene.

4. The perfume composition of claim 1 wherein the compound is 2,6,6-Trimethyl-1-[buten-3-oyl]-1,4-cyclohexadiene.

5. The perfume composition of claim 1 wherein the compound is 2,6,6-Trimethyl-1-[buten-3-oyl]-2,4-cyclohexadiene.

6. The perfume composition of claim 1 wherein the compound is cis- and trans-2-Methylene-6,6-dimethyl-1-[buten-2-oyl]-3-cyclohexadiene.

7. The perfume composition of claim 1 wherein the compound is 2-Methylene-6,6-dimethyl-1-[buten-3-oyl]-3-cyclohexadiene.

* * * * *